United States Patent [19]

Walfield et al.

[11] Patent Number: 4,652,628

[45] Date of Patent: Mar. 24, 1987

[54] METHODS AND COMPOSITIONS FOR EXPRESSION OF BTI ENDOTOXIN

[75] Inventors: Alan M. Walfield; Thomas J. Pollock, both of San Diego, Calif.

[73] Assignee: Syntro Corporation, San Diego, Calif.

[21] Appl. No.: 693,556

[22] Filed: Jan. 22, 1985

Related U.S. Application Data

[63] Continuation-in-part of Ser. No. 582,506, Feb. 22, 1984.

[51] Int. Cl.[4] .................................................. C07K 7/10
[52] U.S. Cl. ...................................... 530/324; 530/350
[58] Field of Search .................... 514/12; 260/112 SR; 530/324, 350

[56] References Cited

U.S. PATENT DOCUMENTS 4,467,036  8/1984  Schnepf et al. .................. 435/172.3

OTHER PUBLICATIONS

FEBS, 0549, vol. 158, No. 1 (1983), Ward et al.
Proc. Nat'l. Acad. Sci., vol. 79, 6951-55 (1982), Gonzalez et al.
Gene 33, (1985), 151-158, Sekar et al.
FEBS 1820, vol. 175, No. 2 (1984), Ward et al.
Proc. Nat'l. Acad. Sci., 78 (1981), 2893-2897, Schnepf et al.
Symposium on *Bacillus thuringiensis*, var. *israelensis*, H-14 (1982).

*Primary Examiner*—Delbert R. Phillips
*Attorney, Agent, or Firm*—Bertram I. Rowland

[57] ABSTRACT

DNA sequences are provided coding for *Bacillus thuringiensis* var. *israelensis* (BTI) endotoxin, employing bacterial hosts which produce a protein having insecticidal activity for dipteran insects.

The bacteriophage lambda strain SYN A4-1 was deposited at the A.T.C.C. on Feb. 22, 1984 and given Accession No. 40098.

4 Claims, No Drawings

METHODS AND COMPOSITIONS FOR EXPRESSION OF BTI ENDOTOXIN

CROSS-REFERENCE TO RELATED APPLICATIONS

This application is a continuation-in-part of application Ser. No. 582,506, filed Feb. 22, 1984, which disclosure is incorporated herein by reference.

BACKGROUND OF THE INVENTION

1. Field of the Invention

The ability to isolate DNA sequences coding for naturally occurring polypeptides and introducing the isolated sequences into foreign hosts for expression of the encoded polypeptide has greatly expanded the opportunities to produce polypeptides or analogs thereof having biological activity. As more is learned about the mechanism of expression in both prokaryotes and eukaryotes, there is an expanding appreciation of the sophistication of the mechanisms of transcription and translation, as well as replication, and the interaction of naturally occurring segments, both coding and non-coding. While various techniques have been developed which aid in the isolation, sequencing and synthesizing of DNA and peptides, each investigation of expression of a new polypeptide frequently results in unanticipated obstacles, which require new approaches or modifications of existing techniques.

It has long been known that *B. thuringiensis* species produce a variety of proteins having insecticidal activity. Because of their natural nature, biodegradability, and the apparent absence of insect resistance to their toxicity, these insecticides have attracted much interest. However, due to the difficulties of growing the host for producing the insecticidal protein, the use of these naturally-occurring insecticides has been somewhat limited. It has therefore become of interest to develop DNA sequences coding for proteins having the same or analogous properties to the naturally occurring *B. thuringiensis* insecticides.

The endotoxin is formed in a proform as a crystalline inclusion body. The effectiveness of a soluble form, the possibility of instability to proteolytic or other degradation and the ability to produce active fragments, which may have substantial advantages in economics and activity remain to varying degrees a matter of conjecture.

2. Description of the Prior Art

The *Bacillus thuringiensis* var. *israelensis* (BTI) endotoxin has been suggested to be associated with the large plasmids of this species. Kamdar and Joyaraman, *Biochem. Biophys. Res. Commun.* (1983) 110:477–482; and Clarke et al., (1983) *Abstracts of the Annual Meeting of the American Society for Microbiology:* H91. Properties of BTI endotoxin are described by Thomas and Ellar, *J. Cell Sci.* (1983) 60:181–197; Tyrell et al., *J. Bacteriol.* (1981) 145:1052–1062; and Clarke et al., supra. Properties of the *kurstaki* endotoxin as produced by recombinant plasmids is described in Schnepf and Whitely, *Proc. Natl. Acad. Sci. USA* (1981) 78:2893–2897, reporting that a soluble, rather than crystalline form is obtained.

SUMMARY OF THE INVENTION

Methods are provided for isolating a DNA sequence coding for a polypeptide having toxicity to dipteran insects. Particularly, a strain of *B. thuringiensis* var. *israelensis* is employed as a source of plasmid DNA and the plasmid DNA isolated. From the plasmid DNA, a DNA sequence containing the gene encoding for an insecticidal polypeptide is excised. The DNA sequence, modified sequence, or fragment thereof, is introduced into an appropriate extra-chromosomal vector for introduction into a compatible bacterial host for production of an insecticidal polypeptide having a biological property analogous to the BTI endotoxin.

BRIEF DESCRIPTION OF THE FIGURE

The FIGURE shows a restriction endonuclease map of the BTI DNA of pSY367 (upper portion of FIGURE) and a restriction endonuclease map of pSY408 (lower portion).

DESCRIPTION OF THE SPECIFIC EMBODIMENTS

Novel DNA sequences and constructions are provided for use in methods for expressing insecticidal polypeptides. The insecticidal polypeptides are found to have a biological property(ies) analogous to the endotoxin of *Bacillus thuringiensis* var. *israelensis* (BTI).

In accordance with the method, a strain of BTI is employed as a source for a DNA sequence coding for an insecticidal polypeptide. To enhance the available amount of DNA, the organism is grown at 32° C. in modified SP4 medium to log phase, lysed and plasmid DNA isolated (Kronstad et al., *J. Bacteriol.* (1983) 154:419–428).

The plasmid DNA is then treated in manner to concentrate DNA fragments isolated from large plasmids. A particularly useful method for this purpose is to partially digest the plasmid DNA under mild conditions for a short period of time employing a restriction endonuclease having a recognition sequence of at least four nucleotides. Desirably, the fragments obtained will be from about 10 to 20 kbp in length.

The conditions for the partial digest will generally include times of from about one to five minutes, temperatures of from about 10° to 30° C., more usually of from about 15° to 25° C. and ratios of about 10 to 50 µg plasmid DNA per unit of restriction enzyme. Of particular interest as the restriction enzyme is Sau3AI, although other restriction enzymes may be employed, such as BamHI, HindIII, etc. Other conditions, such as salt concentrations, buffer, and the like, will be those specified by the supplier.

The resulting mixture of linear and circular DNA is then isolated in accordance with conventional ways, e.g., extraction with phenol and chloroform followed by precipitation with ethanol.

The resulting DNA may be introduced into any convenient cloning vector, only the linear DNA being capable of ligation. Alternatively, linear DNA may be enriched by gel electrophoresis, gradient centrifugation, or the like, prior to insertion into a vector.

A large number of cloning vectors for fragments of 10 to 20 kbp are available and may be used. Illustrative cloning vectors include lambda, Charon 4A, pBR322, EMBO-4, or the like. Usually, for cloning, it is convenient to use a strain of *E. coli*, where the bacteria can be grown to high density and the vector allows for selection. Thus, the desired sequence can be obtained in relatively large amounts for subsequent manipulation. A wide variety of markers are known which provide complementation, e.g., prototrophy in an auxotrophic host; biocide resistance, e.g., antibiotics, toxins, heavy metals, etc.; immunity, or the like.

Due to recognition by *E. coli* of transcriptional and translational regulatory signals associated with the BTI endotoxin, the clones resulting from the transformants or transfectants may be screened for the expression of a polypeptide having immunogenic properties analogous to the naturally occurring BTI endotoxin. Therefore, to simplify the screening method, one may prepare antibodies in accordance with conventional ways, either polyclonal or monoclonal, which specifically recognize the BTI endotoxin. The antibodies may be absorbed with proteins from the host to reduce the potential of cross-reactivity, which would result in false positive clones. Conveniently, the host or host proteins may be bound to a convenient support and the antiserum contacted with the antigens and unbound antiserum isolated.

The clones may then be screened with the antiserum, followed by labeling the bound antiserum with an appropriate label. Conveniently, the antibodies bound by the clones may be labeled with a radioisotope, enzyme, or fluorescer, as desired and is conventional in the field. The plaques or the colonies of individual clones may be contacted with the antibody. By having the antigens present in the host fixed to a support, after washing away non-specifically-bound antibodies and label, the label at a particular site will indicate the presence of the endotoxin. Usually, the clones are grown on an agar nutrient medium and lysed (if required), followed by contacting the clones with an indexed filter, e.g., nitrocellulose filter, so as to transfer a portion of the clone-encoded proteins to the filter. In this way, the particular clones showing positive results may be located from the site on the filter.

Clones which have been detected to have a positive immune response to the BTI endotoxin antiserum may then be grown and the cells or lysates tested for insecticidal activity. The insecticidal activity can be demonstrated by combining the cells or lysates with larvae of an insect known to be sensitive to BTI endotoxin. An illustrative insect is *Aedes aegypti.*

Various organisms may be employed for expressing the polypeptide having biological activity analogous to BTI endotoxin. Illustrative hosts include *E. coli, B. megaterium, B. stearothermophilus, B. subtilis,* or the like; that is, bacteria which can provide for transcription and translation of the insecticidal polypeptide, particularly those bacteria which can recognize the transcriptional and translational regulatory signals recognized by *B. thuringiensis,* more particularly Bacillus organisms other than the source of the endotoxin, i.e., *B. thuringiensis.*

If desired, the large fragment obtained by partial digestion may be further manipulated to provide for a smaller fragment, which may retain some or all of the regulatory signals associated with expression or some or all of the regulatory signals may be substituted or augmented, and/or all or part of the polypeptide coded for by the gene, retaining an active polypeptide. Manipulation may involve partial or complete digestion with one or more restriction enzymes, whereby the resulting fragments, generally ranging from about 500 to 5,000 bp may be cloned and screened for the presence of the desired gene. Screening may include DNA probes, expression in expression vector systems, cells inactivated with ultra-violet radiation, in vitro translation, immunoprecipitations, screening for messenger RNA, or the like.

The structural gene with its 5'- and 3'-flanking untranslated regions which include transcriptional and translational initiation and termination regulatory regions, respectively, may be manipulated in a variety of ways. Regions may be removed by restriction endonuclease digestion with ligation of particular fragments, as appropriate. For removal of terminal sequence, where the number of base pairs removed may be varied, resection with an exonuclease may be employed. For removal of sequences and/or changes in one or more base pairs, which may be silent or result in one or more amino acid changes, in vitro mutagenesis, primer repair, and/or ligation with adapters, linkers, or the like, may be employed. Thus, the polypeptides of this invention may include the intact proform, a fragment which includes none or a portion of the sequence which is naturally deleted, or a fragment which includes all or only an active portion of the mature toxin. For the purposes of the invention the term toxin shall include any active fragment or the entire toxin, whether in the mature or proform.

Of particular interest are polypeptides of at least about 50 kD (kilodaltons) up to the 100 kD, usually at least about 55 kD, preferably with fragments of about 50 to 65 kD, where the N-terminal amino acids are at least substantially the same (fewer than about 5 amino acid differences) as the natural or wild type BTI. Desirably, the detection beginning from the 3'-end of the coding sequence of the coding strand should not extend beyond the second AccI site, usually not extend beyond the second AccI site, more usually not extend beyond the PstI site, more particularly not extend beyond the XbaI site in the 3'- to 5'-direction of the coding strand, where the region in the 5'-3' direction has the following restriction sites in the order HindIII-XmnI-XhoI-BglII-AccI*-StuI*-PstI-XbaI*-AccI, where the specified restriction sites are indicated by an asterisk.

While in many bacterial hosts it will be sufficient to retain the 5'-untranslated region for the transcriptional initiation regulation, for many purposes it will be desirable to provide an alternative transcriptional regulation region. Other transcriptional regulation regions may provide for higher production of the toxin, regulated expression, such as by temperature, metabolite, or the like, or other property of interest. By cleaving upstream from the ribosomal binding site or upstream from the initiation codon, the wild-type untranslated 5'-region may be substituted with a different 5'-region which provides for transcriptional and translational regulation.

The expression product may be produced in a variety of forms, which may include soluble protein, which is secreted or retained by the organism or the protein may form inclusion bodies in the host organism. For secretion, various constructions may be employed, where the gene coding for the BTI endotoxin is inserted downstream and in reading frame with host secretory leader and processing signals; in this way, the resulting polypeptide may be secreted and processed and obtained in the nutrient medium. See, for example, Palva et al., *Gene* (1983) 22:229–235. Alternatively, the protein may be formed in the cytoplasm of the host and retained in the cytoplasm, where it may remain in soluble form or form inclusion bodies and the organism used or lysed and the protein isolated.

The host may be lysed by conventional ways, e.g., detergents, enzymatic degradation, or the like, and the protein isolated and purified by chromatography, electrophoresis, extraction, or the like. The protein may then be used as an insecticide. Alternatively, the organisms may be harvested and dried and used without further modification.

For many, if not most, purposes, it will be sufficient to use the intact host cell containing the toxin as the pesticide. Thus, the cells from the fermentor, including cellular debris and some free toxin may be harvested, dried and formulated. In some instances it will be desirable to separate the toxin from the cells and cellular debris. In this case, the cell may be lysed, cellular debris separated from protein, either soluble or insoluble, and the toxin isolated. Usually, the resulting composition will have at least 50 wt. percent of the toxin, more usually at least 75 wt. percent, preferably at least 90 wt. percent. In view of the use of the toxin, contamination by host proteins or other components is permissible, so that the toxin will rarely be purer than about 99.9%.

The BTI endotoxin may be formulated in a variety of ways, being incorporated with a variety of additives, depending upon its particular use, being formulated as a wet or dry formulation. The endotoxin may be formulated with wetting agents, detergents, stabilizers, adhering agents, spreading agents, extenders, other insecticides, or the like. Usually, the endotoxin will be at least about 0.1% and not more than about 100% by weight of the formulation, more usually of from about 0.15 to 0.8 weight percent of the formulation, as described in Lacey et al., *Tropen Med. Parasit.* (1982) 33:97–101.

The following examples are offered by way of illustration and not by way of limitation.

EXPERIMENTAL

The gene for the BTI endotoxin was isolated from *B. thuringienesis* var. *israelensis* strain ONR-60A, grown to late log phase. The plasmids were isolated and purified by alkaline lysis procedure, followed by successive precipitations with sodium acetate, isopropanol and ethanol (Birnboim and Doly, *Nucleic Acids Res.* (1979) 7:1513). The closed circular plasmids were freed from chromosomal DNA by banding to equilibrium through CsCl density gradients containing ethidium bromide. The plasmid DNA was partially digested with the restriction endonuclease Sau3AI, where the BTI plasmid DNA was incubated with Sau3AI for three minutes at 21° at a DNA to enzyme concentration of 20 μg plasmid DNA to one unit Sau3AI, with salt and buffer concentrations as specified by the supplier, Bethesda Research Laboratories. The conditions minimized cleavage of small plasmids, while providing linear fragments from the large plasmids of from about 10 to 20 kbp. Digestion was terminated by the addition of an equal volume of phenol saturated with the aqueous buffer.

The Sau3AI digest was freed of proteins by successive extractions with phenol and chloroform, followed by precipitation in two volumes of ethanol. The linear BTI DNA was then dissolved in Tris buffer (10 mM, pH 8.0) containing EDTA (1 mM), and ligated with T4 DNA ligase (New England Biolabs) to BamHI-cleaved DNA segments from the bacteriophage cloning vector λL47.1 (Loenen and Brammar, *Gene* (1980) 10:249–259). The recombinant DNA was packaged in vitro into infectious phage particles that were then used to infect *E. coli* strain Q359, a P2 lysogen.

All the plaques resulting from this procedure represented clones with recombinant genomes (Loenen and Brammar, supra). These plaques were then screened for the expression of BTI antigens by an in situ radioimmunoassay (Walfield et al., *Science* (1982) 216:522–523). The immunological screening was performed with rabbit antiserum raised against purified BTI endotoxin. The endotoxin had been obtained from sporulating cultures of BTI that were harvested and washed in a salt solution. The endotoxin-containing crystals were prepared by centrifugation. BTI crystals were purified by sedimentation to equilibrium in sodium bromide density gradients. The antigen for injection into rabbits was equal parts crystals and alkali-solubilized crystals, which had been neutralized with acid. Rabbits were injected with antigen on days 1, 14 and 21 and the immune sera collected on day 28. The sera were specific for BTI and not *B. thuringiensis* var. *kurstaki* crystal preparations. Prior to use in screening plaques of the λL47.1-BTI recombinants, a BTI rabbit antiserum was treated with an *E. coli* immunoabsorbent made by linking the antigens of an *E. coli* Q359 sonicated lysate to CNBr-activated Sepharose 4B beads (Pharmacia Fine Chemicals). This treatment removed most immunoglobulins which bound to *E. coli* antigens from the rabbit serum.

The antigenic selection procedure on recombinant plaques yielded eleven clones which were specifically reactive with BTI antisera. One of the clones selected for further testing was designated BTI A4-1. The assay employed was a modification of that described by Tyrell et al., *Appl. Environ. Microbiol.* (1979) 38:656–658. In this assay, a number of third instar larvae of *Aedes aegypti* are placed in separate containers in a small volume of water. The lysate is administered in the water and the mosquitoes are incubated at room temperature for three to six days, at which time mortality is observed. The *E. coli* lysates are prepared by infecting the host bacteria with the phage clones and growing overnight. The lysates are precipitated with acetone, followed by resuspension and dialysis in 20 mM Tris-HCl, pH 8. This procedure results in a two-fold concentration of a lysate. Larvae incubated in the lysates of BTI A4-1 displayed a markedly higher mortality after three to six days than did larvae incubated in lysates of the cloning vector λL47.1, as well as lysates of some of the other recombinant phage clones. The endotoxin is likely to be produced in a soluble, rather than crystalline form, as was observed with the *kurstaki* recombinant plasmids (Schnepf and Whitely, supra). The soluble form has been found to have a lower toxicity than the crystalline toxin (Thomas and Ellar, supra).

The presence of the BTI endotoxin was also shown by analysis of the proteins produced by the A4-1 lysate of *E. coli*. The polypeptides in an ammonium sulfate precipitated fraction from the clone were compared to polypeptides found in a lysate of λL47.1 and in BTI crystals. The lysate proteins and crystal proteins were analyzed by electrophoretic transfer to a nitrocellulose filter after sodium dodecyl sulfatepolyacrylamide gel electrophoresis. The nitrocellulose filter was then reacted with the immunoabsorbed BTI antiserum and probed with $^{125}$I-labeled *S. aureus* protein A (Walfield et al., supra).

An autoradiograph of the electrophoretic blot showed that the ammonium sulfate precipitant from BTI A4-1 lysate contained at least one polypeptide that was specifically reactive with the BTI antiserum. The BTI A4-1-encoded polypeptide displayed a mobility in the polyacrylamide gel of 100,000 Daltons. This antigen from the clone displayed a reactivity with the BTI antiserum comparable to that of the polypeptides originating from BTI crystals. This reactant was not observed in the λL47.1 lysate. Toxicity to mosquito larvae was associated with this ammonium sulfate precipitated polypeptide by our bioassay. At 45 hr, larvae of *Aedes aegypti* displayed 89% mortality in the ammonium sulfate precipitated fraction of BTI A4-1 lysate in contrast to 11% mortality in a similarly processed fraction from phage L47.1.

TABLE 1

Mortality of *A. aegypti* larvae in BTI A4-1 ammonium sulfate precipitant at 45 hours.

| Sample | Protein Conc. | # A-live | # Dead | % Mortality |
|---|---|---|---|---|
| Amm. Sulf. ppt. BTI A4-1 A | 100 μg/ml | 0 | 3 | |
| Amm. Sulf. ppt. BTI A4-1 B | 100 μg/ml | 0 | 3 | |
| Amm. Sulf. ppt. BTI A4-1 C | 100 μg/ml | 1 | 2 | |
| Totals | | 1 | 8 | 89% |
| Amm. Sulf. ppt. L47.1 A | 100 μg/ml | 3 | 0 | |
| Amm. Sulf. ppt. L47.1 B | 100 μg/ml | 3 | 0 | |
| Amm. Sulf. ppt. L47.1 C | 100 μg/ml | 2 | 1 | |
| Totals | | 8 | 1 | 11% |
| BTI Crystals A | 5 μg/ml | 0 | 3 | |
| BTI Crystals B | 5 μg/ml | 0 | 3 | |
| BTI Crystals C | 5 μg/ml | 0 | 3 | |
| Totals | | 0 | 9 | 100% |

Analysis of the DNA of BTI A4-1 demonstrates that the source of the gene for the BTI toxin is the recombinant clone. The BTI-specific polypeptide was identified among the products from an in vitro translation of BTI A4-1 DNA. For this procedure, *E. coli* host cells were killed by irradiation with ultra-violet light prior to infection with BTI A-4-1 DNA, as described by Jaskunas et al., *Nature* (1975) 257:458. Only clone-encoded polypeptides were labeled with $^{35}$S-methionine during the in vitro translation. The $^{35}$S-labeled endotoxin of BTI, as expressed by the A4-1 genome was immunoprecipitated with the rabbit anti-serum to BTI crystals. The immunoprecipitated polypeptide was visualized by polyacrylamide gel electrophoresis followed by autoradiography of the gel. This antigen expressed in vitro by A4-1 DNA appeared to be the same 100,000 Dalton antigenic polypeptide seen on the immunoblot of proteins isolated from the phage A4-1 lysate of *E. coli*. A DNA hybridization experiment demonstrated that clone BTI A4-1 includes DNA homologous to a large plasmid of *B. thuringiensis* var. *israelensis*. The BTI plasmid DNA was electrophoresed through an agarose gel and blotted onto nitrocellulose (Southern, J. Mol. Biol. (1975) 98:503-517). The blot was then probed with $^{32}$P-labeled DNA of clone BTI A4-1. Autoradiography of the blot showed that the labeled DNA hybridized to sequences of a large BTI plasmid of a length greater than 50 kbp. Hybridization of the cloned DNA to the BTI plasmid DNA can be attributed to clone A4-1 containing the gene for the delta-endotoxin of BTI which is known to be on a large plasmid (Kamdar and Joyaraman, supra; Clarke et al., supra; Gonzalez and Carlton, Plasmid (1984) 11:28-38). Restriction endonuclease analysis on agarose gels of BTI A4-1 DNA reveals that the clone contains a segment of foreign DNA approximately 11 kbp long. This was named "SYNA4-1".

The cloned gels for the BTI endotoxin was then more extensively characterized, and the level of expression of this gene improved by subcloning fragments of SYNA4-1 into plasmids. The plasmid clone pSY366 was constructed by excising the central EcoRI fragment from the BTI DNA of SYNA4-1 and inserting it into the EcoRI site of the plasmid vector pUC13 with T4DNA ligase. The recombinant plasmids were transformed into *E. coli* and the transformants screened for pSY366 as described by Vieria and Messing, *Gene* (1982) 19:259-268. A restriction map of pSY366 was assembled. The pSY366 construct was further reduced in size by excising from it a blunt-ended fragment with the restriction endonucleases HpaI and SmaI and reinserting this fragment into the SmaI site of PUC13. The resultant product, transformed into *E. coli*, was called pSY367. *E. coli* transformants bearing pSY366 or pSY367 display detectable levels of toxicity to larvae of *A. aegypti*.

A 3756 bp long portion of the BTI insert of pSY367 was sequenced. This sequence contains only one open reading frame of a length sufficient ot encode a toxic polypeptide of a size 50 to 100 kD. The reading frame has a stop codon at base pair 2968 and several possible initiation codons, the one most distant from the stop being a base pair 926. Therefore, this open reading frame has the capacity to code for a protein of a maximum size of 76 kD. When stop codons present outside this open reading frame are taken into account, and when the expression of toxin by the deletion mutant pSY408 is considered, there cannot be room anywhere else in clone pSY367 for the toxin gene.

The following is the complete open reading frame sequence with 5'- and 3'-flanking regions of the pSY367 insert.

| | 10 | 20 | 30 | 40 | 50 | 60 | 70 |
|---|---|---|---|---|---|---|---|
| | TTTTTTCTTC | CATATTGAT | AGATTAGCTG | GCCATATTCA | TGAACCCAAC | GCATGATCGT | TGTGGGATGA |
| | 80 | 90 | 100 | 110 | 120 | 130 | 140 |
| | TCTGACACAC | CACGTTCCTG | AAAAATCTCA | GATACATCAC | GATAGCTTAA | AGAAAAACGA | CAGTAATAMC |
| | 150 | 160 | 170 | 180 | 190 | 200 | 210 |
| | AATGGCTACT | AAAATAATGT | CTTTCTTGAA | CTGTTTTCCT | TTAAAATATC | TCATGTAGCA | TTCTCCTCAG |
| | 220 | 230 | 240 | 250 | 260 | 270 | 280 |
| | CACATTTTCC | CTACAGTCTC | CTTTTTCGTG | GAATGGGCAA | AACATCCTG | CTACCGAAAC | GCTGGATTGT |
| | 290 | 300 | 310 | 320 | 330 | 340 | 350 |
| | GGAACAAACT | TTTTCTTAAT | TAGAAAACTA | CCGCAGAACTA | CGGAAGAACT | GTGAGTAAAC | ACTTGAAAAT |
| | 360 | 370 | 380 | 390 | 400 | 410 | 420 |
| | AGTAGACAGA | GTTGCTTATT | GGCATCTGTG | GTGATTTTAT | TAAAAAGATT | CTAGATAGGT | TCTAAGGGTG |
| | 430 | 440 | 450 | 460 | 470 | 480 | 490 |
| | AAGTAGGGAA | ATGGATACCT | TTGTGCAAAC | AGGAGGGGTT | TATGAACCGC | TGTGGTCTGG | AGTTAGAACG |
| | 500 | 510 | 520 | 530 | 540 | 550 | 560 |
| | TGGATGGATG | AGAAGGGCTG | GTATTATGAA | GTGAGACAAA | CAATGTGAAC | AGGATATCTT | CCATCCAAGA |
| | 570 | 580 | 590 | 600 | 610 | 620 | 630 |
| | TGTCCTGTTT | TCTCGTACTC | TCTACTATGG | TTGGACTCAA | AACGCTTATA | GAAGAATTTG | AGGATGTTGA |
| | 640 | 650 | 660 | 670 | 680 | 690 | 700 |
| | AGGGGATAG | GAGGCGATTT | GATATATTTT | TGGGAAATGT | AAAGGTTGAT | TGTCGGAAAA | TGATGAGGTT |
| | 710 | 720 | 730 | 740 | 750 | 760 | 770 |
| | ATTTGTAGAA | AAGATGTAAC | AGGAATACAT | ATAGAAAAAT | ACGAATACTT | TAAAATGCAT | AAGACATATT |
| | 780 | 790 | 800 | 810 | 820 | 830 | 840 |
| | GAAAAAAGA | TGATCAATCA | CTACATAGGA | ATATCCTATA | GGATTTGCGA | AAATGATAAA | TTATGTACAG |
| | 850 | 860 | 870 | 880 | 890 | 900 | 910 |
| | ATAGGTTCTT | GTTAAGTCAT | ATGAATTAAA | AAATGCTTTA | | | GAAAAGAGTT |
| | 920 | | | | | 955 | |
| | GTGTCTAATT | TGAGT | ATG MET | GGA Gly | ATA Ile | TAT Tyr | AAT Asn | CAA Gln | AAT Asn | GAA Glu |

| 970 | | | | | | 1000 | | | 1015 | |
|---|---|---|---|---|---|---|---|---|---|---|
| TAT Tyr | GAA Glu | ATA Ile | TTC Phe | AAT Asn | CCA Pro | AAT Asn | TTT Phe | TCT Ser | AAG Lys | TAT Tyr |

| | | | | 1030 | | | | 1045 | | | | | 1060 | | |
|---|---|---|---|---|---|---|---|---|---|---|---|---|---|---|---|
| AGA Arg | GAA Glu | TAT Tyr | ATA Ile | CCA Pro | TTA Leu | AAT Asn | GCT Ala | TCC Ser | CCA Pro | AGC Ser | AAG Lys | AAC Asn | AAT Asn | TAT Tyr |

| | | | | | | | | 1075 | | |
|---|---|---|---|---|---|---|---|---|---|---|
| GAT Asp | TAT Tyr | TGG Trp | CTC Leu | CCA Pro | GCA Ala | AAT Asn | AAG Lys | CAA Gln | AAA Lys | TAC Tyr |

| | | | 1090 | | | | | 1105 | | |
|---|---|---|---|---|---|---|---|---|---|---|
| TTT Phe | TGG Trp | TGG Trp | GTG Val | GAA Glu | TGT Cys | CAA Gln | CAA Gln | AAT Asn | GGC Gly | GGG Gly |

| | | | | | | 1120 | | 1135 | | |
|---|---|---|---|---|---|---|---|---|---|---|
| ACT Thr | ATG MET | GCT Ala | GAA Glu | GCT Ala | TCT Ser | GAT Asp | GCT Ala | ACG Thr | AAT Asn | GTA Val |

| | | | | 1150 | | | | 1165 | | |
|---|---|---|---|---|---|---|---|---|---|---|
| ACT Thr | ACT Thr | GCT Ala | TTG Leu | CCG Pro | TTT Phe | TTT Phe | GCC Ala | GTT Val | TAT Tyr | GGT Gly |

| | | | | | 1180 | | | | | |
|---|---|---|---|---|---|---|---|---|---|---|
| GGG Gly | TTG Leu | TTG Leu | ATC Ile | ATC Ile | GGA Gly | GGA Gly | TGG Trp | TTC Phe | GCA Ala | GGT Gly |

| | | | | | | | | | 1195 | |
|---|---|---|---|---|---|---|---|---|---|---|
| TCT Ser | GGG Gly | GTA Val | GAT Asp | AAC Asn | CCG Pro | ATC Ile | TTT Phe | GGA Gly | GAT Asp | GCA Ala |

| | | | | | | 1210 | | | | 1225 |
|---|---|---|---|---|---|---|---|---|---|---|
| GAT Asp | GAC Asp | CCT Pro | GAA Glu | ATT Ile | ATA Ile | AAT Asn | AAA Lys | ATT Ile | GGT Gly |

| 1240 | | | | 1255 | | | | | | 1270 |
|---|---|---|---|---|---|---|---|---|---|---|
| ACT Thr | ATG MET | ACT Thr | TTG Leu | ATC Ile | TTT Phe | TAT Tyr | AAT Asn | TTA Leu | TCT Ser | CAA Gln |

| | | | | | | 1285 | | | | |
|---|---|---|---|---|---|---|---|---|---|---|
| GGG Gly | ACT Thr | TTG Leu | CCG Pro | TGG Trp | AGG Arg | AGC Ser | TGG Trp | ATA Ile | GTT Val | AAC Asn |

| | | | 1300 | | | | 1315 | | | |
|---|---|---|---|---|---|---|---|---|---|---|
| GGG Gly | TTG Leu | TTA Leu | CAA Gln | AAT Asn | CCT Pro | GAC Asp | AGG Arg | GAA Glu | TTG Leu | GAT Asp |

| | | | | | | 1330 | | 1345 | | |
|---|---|---|---|---|---|---|---|---|---|---|
| GAT Asp | AAC Asn | ATC Ile | AAC Asn | GGA Gly | ATA Ile | CCT Pro | GAC Asp | AAA Lys | CAG Gln | ATT Ile |

| | | | | 1360 | | | 1375 | | | |
|---|---|---|---|---|---|---|---|---|---|---|
| AAT Asn | GTA Val | ACT Thr | TCT Ser | CTA Leu | ATC Ile | ATA Ile | CAA Gln | AAT Asn | GAT Asp | CAA Gln |

| | | | | | | | 1390 | | | |
|---|---|---|---|---|---|---|---|---|---|---|
| | | | | | | | AAA Lys | GAT Asp | TAT Tyr | CAA Gln |

-continued

| | | | | | | | | | |
|---|---|---|---|---|---|---|---|---|---|
| GAA Glu | TTT Phe 1405 | TTC Phe | GAT Asp 1465 | AAA Lys | CCA Pro | GAG Glu 1420 | ACA Thr | CGT Arg | GCA Ala 1480 | AAT Asn 1495 | GCT Ala | CAC His 1435 | GCT Ala | AAA Lys | GCA Ala 1450 | GTA Val |
| CAT His 1510 | GAT Asp | CTC Leu | TTT Phe | ACT Thr | GAA Glu | TTA Leu | ATA Ile 1540 | ATA Ile | GAT Asp | GAT Asp 1555 | ATG MET | TTA Leu |
| AAA Lys | AAT Asn 1570 | AAT Asn | GCT Ala | AGC Ser | TAT Tyr | CGA Arg | ATA Ile 1585 | CCA Pro | ACA Thr 1600 | CGA Arg | GAT Asp | CAA Gln 1555 | GCA Ala |
| ACT Thr | TGG Trp | CAC His | TTG Leu | AAT Asn 1630 | TAT Tyr | TTA Leu | CAT His | GCT Ala 1645 | TTC Phe | ACC Thr | AAT Asn 1660 | TAC Tyr | TGG Trp |
| CAA Gln | AAT Asn 1675 | CAA Gln | GGT Gly | ATA Ile | CCA Pro 1690 | AGT Ser | ACT Thr | TCA Ser 1705 | TAT Tyr | TCT Ser | GCA Ala | CAA Gln | CAG Gln 1720 |
| TAT Tyr | TTA Leu | TAT Tyr | CGT Arg 1735 | AAA Lys | CAA Gln | GAA Glu | TAT Tyr 1750 | ACT Thr | TGT Cys | TAT Tyr | ACG Thr | TAC Tyr |
| GCA Ala 1780 | GGA Gly | CTA Leu | ATG MET | ACT Thr | ACT Thr | ATA Ile | AAT Asn | GCA Ala | GAT Asp | TAT Tyr | TAT Tyr |
| ACT Thr | TAC Tyr | CGT Arg 1840 | GAA Glu | ATG MET | ACT Thr | CTA Leu 1855 | ACT Thr | CTT Leu 1870 | GCT Ala | GAT Asp | ATA Ile 1765 | TGG Trp |
| AAT Asn | TAT Tyr | ACT Thr | AAA Lys | AAT Asn | CCA Pro | GAT Asp | ATA Ile | TCT Ser | AAA Lys | ACC Thr 1975 | AAC Asn | ATT Ile | GAA Glu | CCA Pro 1885 |
| GTT Val | TAT Tyr 1945 | CTA Leu | GTT Val | AAT Asn | TTA Leu | GAT Asp | GTG Val | GGA Gly 1915 | TTT Phe | ATA Ile | ACA Thr | CAA Gln 2035 | CTT Leu 1930 | GAA Glu |
| GGA Gly | TTA Leu | ATG MET 2005 | GAA Glu 1900 | GAA Glu | CTT Leu | ACT Thr | TTT Phe | ACT Thr | ATA Ile | ATA Ile | AAC Asn | CAA Gln | GGG Gly | TCT Ser |
| ACA Thr 2050 | AGA Arg | TCT Ser | GAC Asp | CCT Pro | TTA Leu | TAT Tyr 2080 | CCT Pro | GAT Asp | ACA Thr | ACA Thr | ATC Ile | CTA Leu | CGT Arg | TTT Phe 2095 | TGG Trp |
| AAC Asn | CAG Gln | GCC Ala | TTT Phe | ACA Thr | CAT His | TTT Phe 2020 | GAT Asp 2065 | AAT Asn | GAT Asp | CAA Gln | GAA Glu | TCA Ser | ATC Ile | ATG MET 2110 | GGA Gly |
| GTT Val | CAT His | GGA Gly | ATT Ile 2170 | GAT Asp | TCT Ser | ATT Ile | CAT His | TCT Ser | ACT Thr 2125 | GAA Glu | GAT Asp | CCT Pro 2200 | TAC Tyr | TAT Tyr | GGA Gly |
| GGA Gly | CCT Pro | TTA Leu | ATT Ile | ATA Ile | CTT Leu | ACT Thr | CAA Gln | GAC Asp | ACA Thr 2185 | GTC Val | TCC Ser | AGA Arg | TCA Ser | GAG Glu | GAT Asp 2260 |
| ACA Thr | AGA Arg | GCC Ala | ATG MET 2275 | AGA Arg | CCT Pro | TAT Tyr | AAT Asn 2290 | AAT Asn | GTC Val | GTC Val 2230 | AGC Ser | AGA Arg | AGA Arg | CGA Arg | TCA Ser |
| AAC Asn | AAA Lys 2215 | CAG Gln | GCC Ala | TTT Phe | AAT Asn 2335 | AAT Asn | AAG Lys | TTT Phe | AAA Lys 2305 | TTT Phe | CAT His 2245 | GAA Glu | TTT Phe | CAT His | CCA Pro |
| ATA Ile | TAT Tyr | GAA Glu | ATA Ile | ATA Ile | ACA Thr 2350 | AGT Ser | ACT Thr | TCT Ser | TAT Tyr | TAT Tyr | GAT Asp | TCA Ser | TAT Tyr | ATT Ile 2365 | GCG Ala 2155 | AGA Arg | ATA Ile | TCC Ser | AAA Lys |
| AAT Asn 2320 | TCA Ser | ACA Thr | CAA Gln | TGG Trp | AAA Lys | AAT Asn | GAA Glu | ACT Thr 2350 | ACT Thr | TAT Tyr | CTA Leu | GGT Gly | CAT His | ACT Thr | ATA Ile | GAT Asp |

| Gln | Thr | Trp 2380 | Lys | Asn | Glu | Glu | Tyr 2395 | Gly | His | Thr | Leu | Ser 2410 | Tyr | Ile | Lys | Thr | Asp 2425 |
|---|---|---|---|---|---|---|---|---|---|---|---|---|---|---|---|---|---|
| AAT Asn | TAT Tyr | ATA Ile | TTT Phe | TCA Ser 2440 | GTA Val | GTT Val | AGA Arg | GAA Glu | AGA Arg 2455 | AGA Arg | AGA Arg | GTT Val | GCA Ala | TTT Phe 2470 | AGT Ser | TGG Trp | ACA Thr |
| CAT His | ACT Thr 2485 | AGT Ser | GTT Val | GAT Asp | TTC Phe | CAA Gln 2500 | AAT Asn | ACA Thr | ATA Ile | TTA Leu 2515 | GAT Asp | AAC Asn | ATC Ile | CAA Gln 2530 | ACC Thr | ATC Ile |
| CAC His | GCT Ala | CTA Leu | AAA Lys 2545 | ACT Thr | TTA Leu | AAG Lys | TCA Ser | AGT Ser 2560 | TCT Ser | CTT Leu | AAA Lys | GAT Asp | ATG MET 2575 | AGT Ser | AAA Lys | GGC Gly | CTC Leu |
| GGT Gly 2590 | CAC His | ACA Thr | AGT Ser | GAA Glu | AAC Asn 2605 | TTG Leu | CAA Gln 2665 | ATT Ile | CTT Leu | GAT Asp | ATT Ile 2575 | CGT Arg 2680 | AAT Asn | TTT Phe 2635 | AGA Arg | GTT Val |
| AGA Arg | TTT Phe | TTA Leu 2650 | AAA Lys | AAT Asn | GTT Val | TCT Ser | CAA Gln 2665 | TTA Leu | TAT Tyr | TAT Tyr | GTA Val | CGT Arg 2680 | ATT Ile | CGT Arg | TAT Tyr | GCT Ala | ACT Thr 2695 |
| AAT Asn | GCT Ala | CCA Pro | AAG Lys | ACA Thr 2710 | GTA Val | GTA Val | TTC Phe | TTA Leu | ACC Thr 2725 | GGA Gly | GAT Asp | AGT Ser | ACT Thr | ATA Ile 2740 | CGT Arg | GTG Val | GAG Glu |
| CTC Leu | CCT Pro 2755 | AGT Ser | ACC Thr | TCC Ser | ACA Thr | CGC Arg 2770 | CAA Gln | AAC Asn | CCA Pro | ACA Thr | GCT Ala 2785 | GAT Asp | TTA Leu | ACA Thr | CAT His | TAT Tyr 2800 | GCA Ala |
| GAT Asp | TTT Phe | GGA Gly | AAA Lys | ACA Thr | GTA Val | TTT Phe | TCA Ser | AAC Asn | AGA Arg 2830 | ACA Thr | TCA Ser | AAT Asn | ACT Thr | CGT Arg | TTT Phe | GAA Glu | GGA Gly |
| GAA Glu 2860 | GAC Asp | TAT Tyr 2815 | GAC Asp | AAT Asn 2875 | GAA Glu | GAA Glu | CCA Pro | TAT Tyr | CCA Pro | CCA Pro | ACA Thr | GAT Asp | CAT His | GTA Val | TCA Ser 2905 | TAT Tyr |
| ATA Ile | TAT Tyr | ATT Ile 2920 | AAA Lys | AAT Asn | ATT Ile | TTT Phe 2935 | GAA Glu | ATT Ile | ATT Ile | CCA Pro | ACT Thr | AAA Lys 2845 | GTA Val | GAT Asp | TTA Leu | TAT Tyr |
| ACA Thr | GAG Glu | AAG Lys | CAA Gln | AAT Asn | AAA Lys 2991 | GAA Glu | GAA Glu | CAG Gln | ACA Thr | ATA Ile | ATC Ile | AAT Asn | CAA Gln 2950 | GAT Asp | TTA Leu | TTA Leu |
| AAT Asn | | | | | | | | | | | | GTG Val | | | | |
| | | | | | | | | | | | | 3011 | | | | |
| AAT Asn | TAA | | | | | | | | | | | | | | | |

| | | | | | | |
|---|---|---|---|---|---|---|
| | | AACAAAGTTC 2981 | TTACTAAAAT 2991 | GCTGTTAAAA 3011 | AGTAAGCGAG 3021 | AAAGGTCGTG 3031 |
| 3041 | 3051 | 3061 | 3071 | 3081 | 3091 | 3101 |
| AACCCTATGT | TTACAAGTGG | TGCGAAAAAT | AGGTTAAAGC | TAGAAACGAC | AGATTATGAA | ATAGATCAAG |
| 3111 | 3121 | 3131 | 3141 | 3151 | 3161 | 3171 |
| TGGCTAATGC | TATAGAATGT | ATGTCAGATG | AACAATATTC | AAAAGAAAAA | CTGATGTTAT | GGGATCAAGT |
| 3181 | 3191 | 3201 | 3211 | 3221 | 3231 | 3241 |
| AAAACATGCA | AAATACCTTA | GTCAGTCTCG | AAATTTGCTT | CAAAATGGTG | ATTTTGAAGA | TGTATTTCAT |
| 3251 | 3261 | 3271 | 3281 | 3291 | 3301 | 3311 |
| GGATGGACTA | CAAGTGATCA | TATGTACATT | CAGTCGGATA | AAAATGGAAT | TAAAGGAAAT | TATCTGAATA |
| 3321 | 3331 | 3341 | 3351 | 3361 | 3371 | 3381 |
| TATCTGGGGC | GCGAGACATA | TACTTAACGA | CAGTCGGATA | ATTCTACTTT | CAAAAAATTG | ATGAATCAAA |
| 3391 | 3401 | 3411 | 3421 | 3431 | 3441 | 3451 |
| ATTAAAACCG | TATACACGTT | ACCTAGTAAG | GGGATTTGTA | ATACATTTAC | AAGATGTAGA | ACTAGTGGTT |
| 3461 | 3471 | 3481 | 3491 | 3501 | 3511 | 3521 |
| TCACGCTATG | GAAAAGAAAT | AGATACAGTC | AGATAGTAC | CATTTGATAT | GGAAGTAGTA | TCTTCTAGGC |
| 3531 | 3541 | 3551 | 3561 | 3571 | 3581 | 3591 |
| CTNTTTGTAA | TGAATTATAT | GATGGTGAAC | AACAACCGTA | ATGTAGGAT | TCCAAATGGG | ATTATAATCC |

-continued

| 3601 | 3611 | 3621 | 3631 | 3641 | 3651 | 3661 |
|---|---|---|---|---|---|---|
| AATGTCAGCT | TTTACGCCTT | CTTACACATC | TGATGCTCGT | CAGTGTATGC | CAAGGAAAAA | ACAGATAGTT |
| 3671 | 3681 | 3691 | 3701 | 3711 | 3721 | 3731 |
| CGTCAAGATT | TTCATCAGTT | TAAGTTTCAT | ATTGATACAG | GTGAAGTAGA | TTATAATACA | AATATAGGGA |

Expression of the BTI DNA of pSY367 was effectively enhanced by transferring it into *Bacillus subtilis.* This transfer was effected by excising the BTI DNA of pSY367 with EcoRI and inserting it into the EcoRI site of the Bacillus cloning vector pUB110 (Gryczan et al., *J. Bacteriol.* (1978) 134:316-329). This plasmid DNA was transformed into *B. subtilis,* and clones containing recombinant plasmids were identified by screening kanamycin resistant clones for those containing plasmids larger than pUB110. Several such clones were isolated. One proved to maintain the insert of BTI DNA in a stable form. This clone contained a plasmid designated pSY408 which had undergone a spontaneously generated deletion around an EcoRI site. Approximately 1.6 kb of BTI 3'-sequences and 0.2 kb of pUB110 were lost. The restriction map of pSY408 is shown in the FIGURE.

Clones containing pSY408 retain the full coding capacity for the BTI endotoxin as evidenced by toxicity in bioassays. *B. subtilis* strains with pSY408 display a potent toxicity to mosquito larvae. Each determination in the bioassays represents 10 fourth instar larvae of *A. aegypti* fed lyophilized cells of *B. subtilis* and observed at 24 hr.

TABLE 2

| Toxicity to Mosquitoes of *B. subtilis* containing pSY408. | | |
|---|---|---|
| % dry weight | | % mortality |
| 0.003 | 20 | 0 |
| 0.006 | 30 | 10 |
| 0.015 | 70 | 30 |
| 0.025 | 80 | 80 |
| 0.06 | 100 | 90 |
| 0.1 | | 100 |

The toxin synthesized by pSY408 strains of *B. subtilis* has been characterized by immunoblot experiments and by a cell-free transcription-translation of pSY408 DNA (Zubay, *Ann. Rev. Genet.* (1973) 7:267-287). Both types of analysis revealed the clone-synthesized product to be a polypeptide of an apparent molecular weight of 58,000 Daltons on polyacrylamide-SDS gels. Immunoblot experiments, similar to the one described for a lysate of SYNA4-1, were performed on ammonium sulfate precipitates from lysed pSY408 *B. subtilis* clones. These blot experiments demonstrated the presence of a 58,000 Dalton antigen, reactive with antiserum to BTI crystals, which was distinctive to pSY408 clones of *B. subtilis.* The cell-free translation showed that the only protein species encoded by pSY408, and not expressed by the vector pUB110, was the 58,000 Dalton polypeptide.

In order to establish an identity between the 58 kD cloned product and the BTI crystal toxin, a more specific antiserum to BTI crystal proteins in denatured form was developed and used in a series of carefully controlled immunoblot studies. This antiserum was raised in two rabbits, as described previously, by injecting them with purified denatured solubilized polypeptides from purified BTI crystals. The polypeptides used for the rabbit immunizations were prepared by dissolving BTI crystals (purified in renografin density gradients) in 50 mM NaOH, 10 mM EDTA, pH 11.8, for 4 days, followed by electrophoresis through a polyacrylamide-SDS gel and electroeluting from the gel only the polypeptides of molecular weight 24-29 kD. Polypeptides of this size were chosen because it has been reported that toxic activity is associated with BTI crystal polypeptides in this size range.

The specific new antiserum was used in immunoblot studies on equivalent quantities of the protein from BTI and BTK crystals, the proteins in 10% ammonium sulfate precipitates of lysates of BTK, clone *B. subtilis*-pSY408, and negative control *B. subtilis*-pUB110. Antibodies in the antiserum bound to all of the polypeptides generated from the BTI crystals, including the largest major crystal proteins of sizes 130 kD and 68 kD, despite the antiserum having been raised only against antigens in the 24-29 kD size rage. This suggests relatedness and possible product-precursor relationships between larger and smaller polypeptides.

This antiserum was approximately 100 times more reactive to immunoblotted BTI crystal polypeptides than prior antiserum which had been raised against native proteins. The new antiserum showed an equally intense immunological reactivity to the 58 kD product of clone pSY408. The antiserum showed no comparable specificity for any 10% ammonium sulfate-precipitated proteins extracted from the *B. subtilis* control strain containing the plasmid vector pUB110, or extracted from BTK cell lysates, nor did antibodies in the serum display any binding to BTK crystal proteins. This observation demonstrated that the antiserum would distinguish a specific immunological similarity between the clone-encoded protein and BTI toxin. This relationship was confirmed by preabsorbing an antiserum mixture with various antigens prior to probing immunoblots with the mixture. The denatured BTI-specific antiserum was mixed with antiserum raised against BTK crystals. When BTI reactants were absorbed out of the BTI-BTK antiserum mixture by a preabsorption step with solubilized BTI crystals, the serum no longer reacted with the BTI crystal proteins or the 58 kD polypeptide of pSY408, while reactivity to BTK crystal antigens was unaffected. The reciprocal experiment was done by preabsorbing the serum mixture with BTK crystal polypeptides which eliminated only the anti-BTK activity. These results showed that the preabsorption step removed only antibodies to homologous antigens. Thus, there is specific immunlogical cross-reactivity between the BTI crystal proteins and the clone product of plasmid pSY408. This relationship was tested by one more preabsorption-immunoblot experiment: The serum mixture was preabsorbed with the denatured 58 kD clone toxin before using it to probe an immunoblot of polypeptides from BTI crystals, BTK crystals, *B. subtilis* with pSY408, and *B. subtilis* with pUB110. The preabsorption with the clone toxin removed the antibodies to the clone protein and to all but one of the BTI crystal polypeptides (a polypeptide at 30 kD), leaving BTK reactants unaffected. This last observation fully authenticates an immunological identity between the clone-synthesized toxin and polypeptides from BTI crystals.

In accordance with the subject invention, novel proteins are produced providing for insecticidal activity against dipteran insects; the proteins are produced by expression of DNA sequences encoding for at least a portion of the BTI endotoxin, where the proteins are produced in other than the native host. By employing other than the native hosts, the insecticidal proteins can be produced economically and efficiently without requiring the complex nutritional requirements of the native host. Thus, a protein which is ecologically-acceptable can be employed for controlling a variety of insect pests.

Although the foregoing invention has been described in some detail by way of illustration and example for purposes of clarity of understanding, it will be obvious that certain changes and modifications may be practiced within the scope of the appended claims.

What is claimed is:

1. A polypeptide composition having insecticidal activity against dipteran insects consisting essentially of the amino acid sequence of the BTI endotoxin as encoded for in pSY367, produced in a unicellular microorganism host other than *B. thuringiensis* var. *israelensis*, and retaining at least a portion of said host.

2. A polypeptide composition according to claim 1, wherein said polypeptide is produced in *E. coli*.

3. A polypeptide composition according to claim 1, wherein said polypeptide is produced in a Bacillus.

4. A polypeptide composition according to claim 1, having a molecular weight in the range of about 50 to 65 kD.